US009393136B2

(12) United States Patent
Perkins et al.

(10) Patent No.: US 9,393,136 B2
(45) Date of Patent: Jul. 19, 2016

(54) VARIABLE ZONE HIGH METAL TO VESSEL RATIO STENT AND METHOD

(75) Inventors: Keith Perkins, Santa Rosa, CA (US);
Samuel Robaina, Santa Rosa, CA (US);
Jeffery Argentine, Petaluma, CA (US);
Walter Bruszewski, Windsor, CA (US);
Andrew Kiehl, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 574 days.

(21) Appl. No.: 13/430,907

(22) Filed: Mar. 27, 2012

(65) Prior Publication Data

US 2013/0261727 A1    Oct. 3, 2013

(51) Int. Cl.
| | |
|---|---|
| A61F 2/06 | (2013.01) |
| A61F 2/04 | (2013.01) |
| A61F 2/915 | (2013.01) |
| A61F 2/07 | (2013.01) |
| A61F 2/90 | (2013.01) |
| A61F 2/91 | (2013.01) |
| A61F 2/848 | (2013.01) |

(52) U.S. Cl.
CPC . *A61F 2/915* (2013.01); *A61F 2/07* (2013.01); *A61F 2/90* (2013.01); *A61F 2/91* (2013.01); *A61F 2002/061* (2013.01); *A61F 2002/065* (2013.01); *A61F 2002/8486* (2013.01); *A61F 2002/91508* (2013.01); *A61F 2002/91516* (2013.01); *A61F 2002/91525* (2013.01); *A61F 2230/0013* (2013.01); *A61F 2250/0018* (2013.01); *A61F 2250/0029* (2013.01)

(58) Field of Classification Search
CPC ............. A61F 2/90; A61F 2/91; A61F 2/915; A61F 2002/8486; A61F 2002/86; A61F 2002/91508; A61F 2002/91516; A61F 2002/91525; A61F 2250/0018; A61F 2250/0029
USPC ................ 623/1.12, 1.15, 1.16, 1.1; 606/200; 43/1.12, 1.15, 1.16, 1.1
See application file for complete search history.

(56) References Cited

U.S. PATENT DOCUMENTS

| | | | |
|---|---|---|---|
| 5,817,126 A | 10/1998 | Imran | |
| 5,817,152 A | 10/1998 | Birdsall et al. | |
| 6,093,199 A | 7/2000 | Brown et al. | |
| 6,190,402 B1 | 2/2001 | Horton et al. | |
| 6,273,910 B1 * | 8/2001 | Limon | ......................... 623/1.15 |
| 6,451,051 B2 | 9/2002 | Drasler et al. | |
| 7,069,835 B2 | 7/2006 | Nishri et al. | |
| 7,093,527 B2 | 8/2006 | Rapaport et al. | |
| 7,163,553 B2 * | 1/2007 | Limon | ......................... 623/1.15 |

(Continued)

FOREIGN PATENT DOCUMENTS

| | | |
|---|---|---|
| WO | 98/47447 A1 | 10/1998 |
| WO | WO98/47447 | 10/1998 |

(Continued)

*Primary Examiner* — Todd J Scherbel

(57) ABSTRACT

A variable zone high metal to vessel ratio stent includes a proximal high metal to vessel ratio zone, a central low metal to vessel ratio zone, and a distal high metal to vessel ratio zone. The proximal high metal to vessel ratio zone is deployed with fixation and sealing to healthy tissue of a main vessel superior to branch vessels and an aneurysm. The central low metal to vessel ratio zone is deployed directly on ostai of the branch vessels. However, as the central low metal to vessel ratio zone is highly permeable, blood flows from the main vessel through the central low metal to vessel ratio zone and into branch vessels.

14 Claims, 8 Drawing Sheets

(56) References Cited

U.S. PATENT DOCUMENTS

| | | | |
|---|---|---|---|
| 7,275,471 B2 | 10/2007 | Nishri et al. | |
| 7,306,624 B2 | 12/2007 | Yodfat et al. | |
| 7,331,987 B1* | 2/2008 | Cox | 623/1.16 |
| 7,572,290 B2 | 8/2009 | Yodfat et al. | |
| 7,588,597 B2 | 9/2009 | Frid | |
| 2002/0013616 A1* | 1/2002 | Carter et al. | 623/1.15 |
| 2003/0109917 A1 | 6/2003 | Rudin et al. | |
| 2003/0204244 A1* | 10/2003 | Stiger | 623/1.16 |
| 2004/0267352 A1* | 12/2004 | Davidson et al. | 623/1.15 |
| 2006/0206201 A1* | 9/2006 | Garcia et al. | 623/1.51 |
| 2007/0010872 A1* | 1/2007 | Gregorich | 623/1.16 |
| 2007/0168018 A1 | 7/2007 | Amplatz et al. | |
| 2007/0265697 A1* | 11/2007 | Goicoechea et al. | 623/1.15 |
| 2009/0259292 A1 | 10/2009 | Bonhoeffer | |
| 2009/0270970 A1 | 10/2009 | Yodfat et al. | |
| 2010/0174358 A1* | 7/2010 | Rabkin et al. | 623/1.16 |
| 2010/0198334 A1 | 8/2010 | Yodfat et al. | |
| 2010/0262217 A1* | 10/2010 | Bruszewski | 623/1.11 |
| 2010/0268326 A1* | 10/2010 | Leynov et al. | 623/1.16 |
| 2011/0137407 A1* | 6/2011 | Nguyen et al. | 623/1.42 |
| 2011/0184507 A1* | 7/2011 | Fischer, Jr. et al. | 623/1.16 |
| 2012/0022578 A1* | 1/2012 | Jantzen et al. | 606/200 |

FOREIGN PATENT DOCUMENTS

| | | |
|---|---|---|
| WO | 03/007840 A2 | 1/2003 |
| WO | WO03/007840 | 1/2003 |
| WO | WO2008/051554 | 5/2008 |
| WO | WO2008/091515 | 7/2008 |

* cited by examiner

VARIABLE ZONE HIGH METAL TO VESSEL RATIO STENT AND METHOD

BACKGROUND

1. Field

The present application relates to an intra-vascular device and method. More particularly, the present application relates to a device for treatment of intra-vascular diseases.

2. Description of the Related Art

A conventional stent-graft typically includes a radially expandable reinforcement structure, formed from a plurality of annular stent rings, and a cylindrically shaped layer of graft material, sometimes called graft cloth, defining a lumen to which the stent rings are coupled. Main stent-grafts are well known for use in tubular shaped human vessels.

To illustrate, endovascular aneurysmal exclusion is a method of using a stent-graft to exclude pressurized fluid flow from the interior of an aneurysm, thereby reducing the risk of rupture of the aneurysm and the associated invasive surgical intervention.

Stent-grafts with custom side openings are sometimes fabricated to accommodate the particular vessel structure of each individual patient. Specifically, as the location of branch vessels emanating from a main vessel, e.g., having the aneurysm, varies from patient to patient, stent-grafts are fabricated with side openings customized to match the position of the branch vessels of the particular patient. However, custom fabrication of stent-grafts is relatively expensive and time consuming.

Further, the stent-grafts must be deployed such that the custom side openings are precisely aligned with the respective locations of the branch vessels. This is a relatively complex procedure thus increasing the risk of the procedure.

SUMMARY

A variable zone high metal to vessel ratio stent includes a proximal high metal to vessel ratio zone, a central low metal to vessel ratio zone, and a distal high metal to vessel ratio zone. The proximal high metal to vessel ratio zone is deployed with fixation and sealing to healthy tissue of a main vessel superior to branch vessels and an aneurysm. The central low metal to vessel ratio zone is deployed directly on ostai of the branch vessels. However, as the central low metal to vessel ratio zone is highly permeable, blood flows from the main vessel through the central low metal to vessel ratio zone and into branch vessels. Further, the distal high metal to vessel ratio zone covers and excludes the aneurysm. As the variable zone high metal to vessel ratio stent is integral, the variable zone high metal to vessel ratio stent is deployed in a single operation which reduces procedure time and complexity.

These and other features of embodiments will be more readily apparent from the detailed description set forth below taken in conjunction with the accompanying drawings.

BRIEF DESCRIPTION OF THE DRAWINGS

In the following description, the same or similar elements are labeled with the same or similar reference numbers.

DETAILED DESCRIPTION

Figure 1:
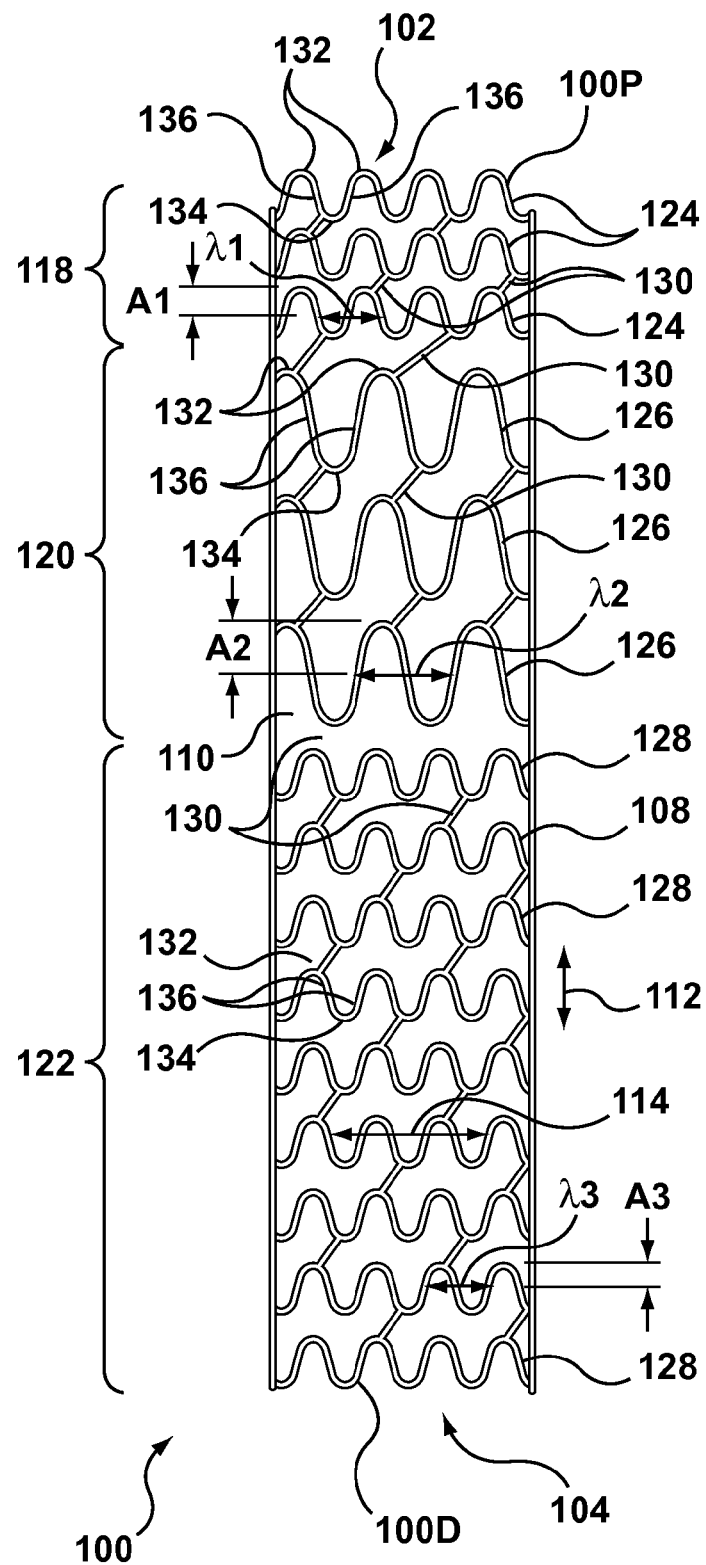
FIG. 1 is a perspective view of a variable zone high metal to vessel ratio stent in its final configuration in accordance with one embodiment.
Figure 2:
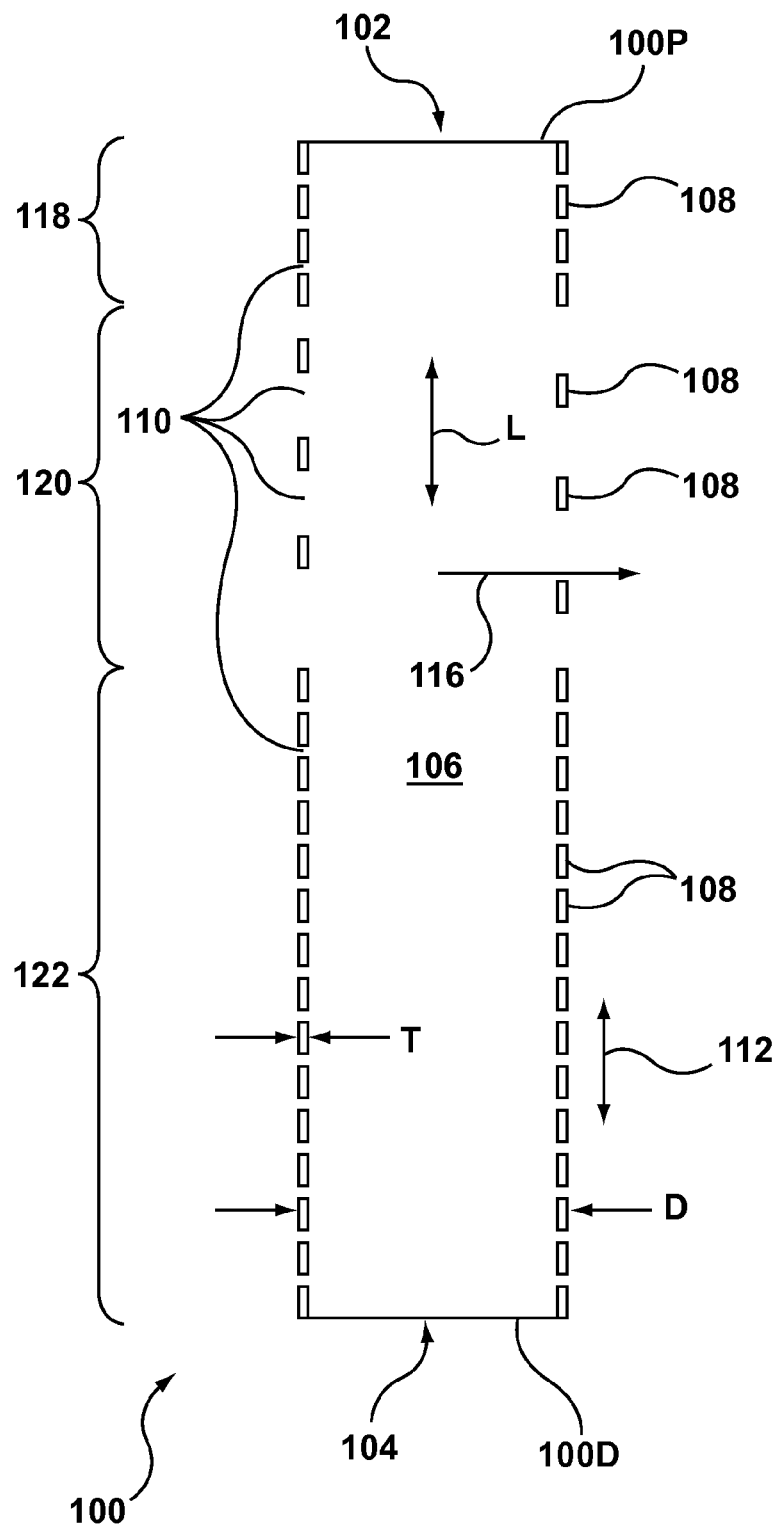
FIG. 2 is a cross-sectional view of the variable zone high metal to vessel ratio stent of FIG. 1.
Figure 5:
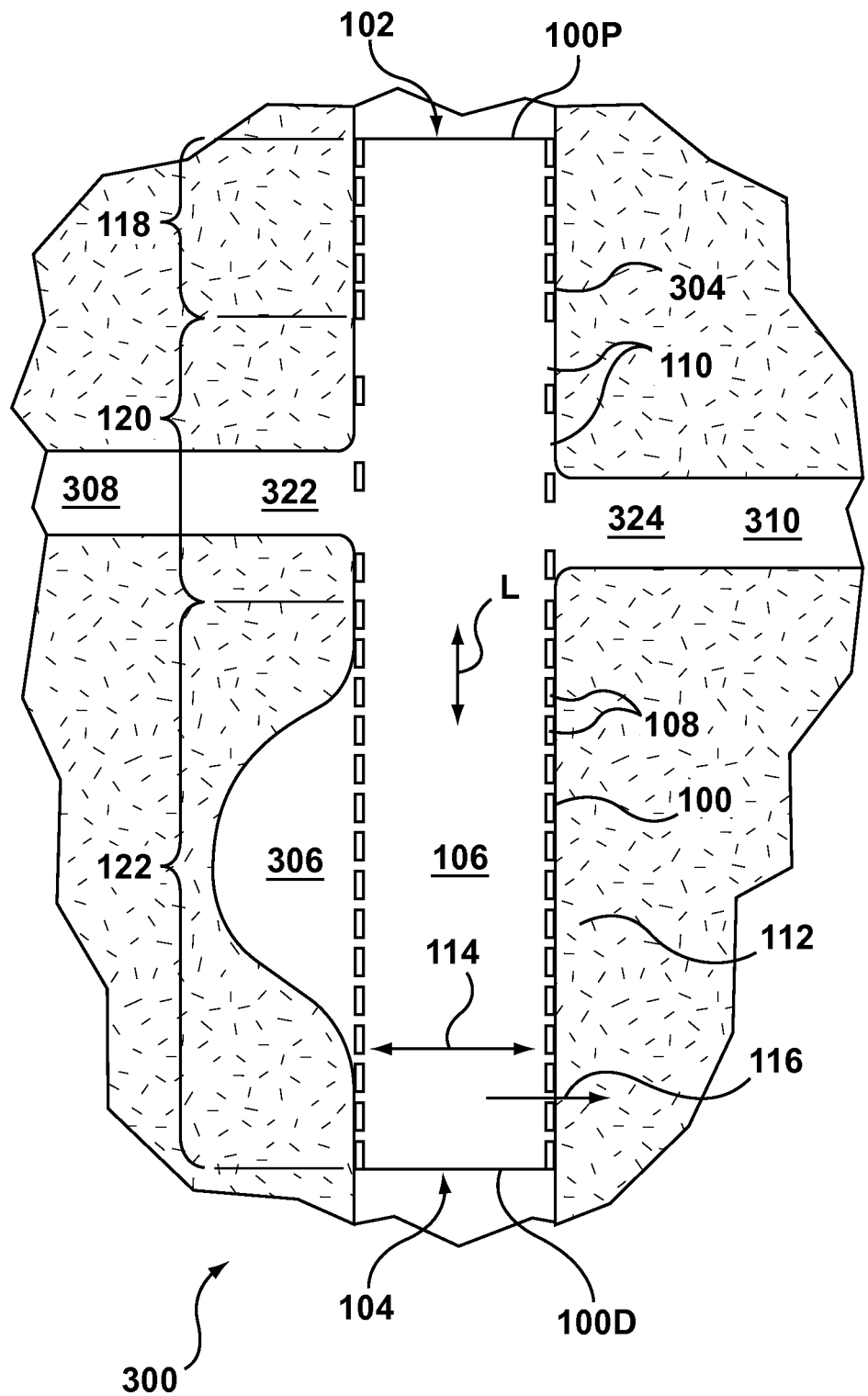
FIG. 5 is a cross-sectional view of the vessel assembly of FIGS. 3 and 4 after deployment of the variable zone high metal to vessel ratio stent of FIGS. 1 and 2 in accordance with one embodiment.

As an overview and in accordance with one embodiment, referring to FIGS. 1, 2, and 5 together, a variable zone high metal to vessel ratio stent 100 includes a proximal high metal to vessel ratio zone 118, a central low metal to vessel ratio zone 120, and a distal high metal to vessel ratio zone 122. Proximal high metal to vessel ratio zone 118 is deployed with fixation and sealing to healthy tissue of a main vessel 304 superior to branch vessels 308, 310 and an aneurysm 306.

Central low metal to vessel ratio zone 120 is deployed directly on ostai 322, 324 of branch vessels 308, 310, respectively. However, as central low metal to vessel ratio zone 120 is highly permeable, blood flows from main vessel 304 through central low metal to vessel ratio zone 120 and into branch vessels 308, 310 thus perfusing branch vessels 308, 310.

Further, distal high metal to vessel ratio zone 122 covers and excludes aneurysm 306. As variable zone high metal to vessel ratio stent 100 is integral, i.e., formed of a single piece and not a plurality of separate pieces connected together, variable zone high metal to vessel ratio stent 100 is deployed in a single operation which reduces procedure time and complexity. This is in stark contrast to deploying multiple stents one within another to vary the metal to vessel ratio of the resulting multi stent arrangement.

Now in more detail, FIG. 1 is a perspective view of a variable zone high metal to vessel ratio stent 100, e.g., an abdominal aortic stent, in its final configuration in accordance with one embodiment. FIG. 2 is a cross-sectional view of variable zone high metal to vessel ratio stent 100 of FIG. 1. Variable zone high metal to vessel ratio stent 100 is sometimes called an endoluminal flow disrupting device.

Referring now to FIGS. 1 and 2 together, variable zone high metal to vessel ratio stent 100 includes a proximal main opening 102 at a proximal end 100P of variable zone high metal to vessel ratio stent 100. Variable zone high metal to vessel ratio stent 100 further includes a distal main opening 104 at a distal end 100D of variable zone high metal to vessel ratio stent 100.

As used herein, the proximal end of a prosthesis such as variable zone high metal to vessel ratio stent 100 is the end closest to the heart via the path of blood flow whereas the distal end is the end furthest away from the heart during deployment. In contrast and of note, the distal end of the delivery system is usually identified to the end that is farthest from the operator (handle) while the proximal end of the delivery system is the end nearest the operator (handle).

For purposes of clarity of discussion, as used herein, the distal end of the delivery system is the end that is farthest from the operator (the end furthest from the handle) while the distal end of the prosthesis is the end nearest the operator (the end nearest the handle), i.e., the distal end of the delivery system and the proximal end of the prosthesis are the ends furthest from the handle while the proximal end of the delivery system and the distal end of the prosthesis are the ends nearest the handle. However, those of skill in the art will understand that depending upon the access location, the prosthesis and delivery system description may be consistent or opposite in actual usage.

Variable zone high metal to vessel ratio stent 100 is cylindrical and includes a longitudinal axis L. A main lumen 106 is defined by variable zone high metal to vessel ratio stent 100 and extends generally parallel to longitudinal axis L and between proximal main opening 102 and distal main opening 104 of variable zone high metal to vessel ratio stent 100.

In accordance with this embodiment, variable zone high metal to vessel ratio stent 100 has a substantially uniform diameter D. However, in other embodiments, variable zone high metal to vessel ratio stent 100 has a non-uniform diameter.

Variable zone high metal to vessel ratio stent 100 is a semi-permeable barrier made of patterned material 108, e.g., is a laser cut single tube or is wire formed and welded. Variable zone high metal to vessel ratio stent 100 includes patterned material 108 and a plurality of holes 110 through which fluid, e.g., blood, can pass.

Generally, variable zone high metal to vessel ratio stent 100 is permeable, sometimes called porous, to fluid, i.e., fluid can pass through variable zone high metal to vessel ratio stent 100 and more particularly, through holes 110. This allows fluid, e.g., blood, to pass through variable zone high metal to vessel ratio stent 100 and nourish, e.g., with oxygen and nutrients, the covered vessel wall. In this manner, hypoxia of the covered vessel wall is avoided. Further, variable zone high metal to vessel ratio stent 100 is permeable to tissue ingrowth.

Longitudinal direction 112 is the direction along variable zone high metal to vessel ratio stent 100 parallel to longitudinal axis L. Circumferential direction 114 is the direction along the circumference of variable zone high metal to vessel ratio stent 100 in plane perpendicular to longitudinal axis L of variable zone high metal to vessel ratio stent 100. Radial direction 116 is along a radius extending from longitudinal axis L in plane perpendicular to longitudinal axis L of variable zone high metal to vessel ratio stent 100.

Generally, there are a plurality, e.g., three or more, of holes 110 arranged in both longitudinal direction 112 as well as circumferential direction 114.

Variable zone high metal to vessel ratio stent 100 includes variable metal to vessel ratio zones 118, 120, 122. Variable metal to vessel ratio zones 118, 120, 122 have different metal to vessel ratios as defined below. Although three variable metal to vessel ratio zones 118, 120, 122 are illustrated and discussed herein, in light of this disclosure, those of skill in the art will understand that variable zone high metal to vessel ratio stent 100 includes more or less than three variable metal to vessel ratio zones in other embodiments.

Variable metal to vessel ratio zones 118, 120, 122 are hereinafter referred to as a proximal, e.g., first, high metal to vessel ratio zone 118, a central, e.g., second, low metal to vessel ratio zone 120, and a distal, e.g., third, high metal to vessel ratio zone 122, respectively.

Proximal high metal to vessel ratio zone 118 is at proximal end 100P of variable zone high metal to vessel ratio stent 100. Distal high metal to vessel ratio zone 122 is at distal end 100D of variable zone high metal to vessel ratio stent 100. Central low metal to vessel ratio zone 120 is between proximal high metal to vessel ratio zone 118 and distal high metal to vessel ratio zone 122.

The ratio of material 108 per unit area of proximal high metal to vessel ratio zone 118 is high, e.g., greater than or equal 30%. This ratio is sometimes called the metal to vessel ratio (or metal to artery ratio) as it defines the percent of the vessel covered with material 108 per unit area of the vessel. Stated another way, the percentage of proximal high metal to vessel ratio zone 118 formed by material 108 is high, e.g., greater than or equal to 30%, and the percentage of proximal high metal to vessel ratio zone 118 formed of holes 110 is low, e.g., less than or equal to 70%.

Generally, the metal to vessel ratio is defined as the area occupied by material 108 of proximal high metal to vessel ratio zone 118 for a unit area of proximal high metal to vessel ratio zone 118 when in the final configuration. To illustrate, for an X square centimeter ($cm^2$) area of proximal high metal to vessel ratio zone 118, Y percent is formed of material 108 whereas Z percent is formed of holes 110, where Y+Z=100. Continuing with this example, Y is the metal to vessel ratio expressed as percent.

To give a specific example for a 40% metal to vessel ratio, for a 1.0 square centimeter area of proximal high metal to vessel ratio zone 118, 0.4 square centimeters would be covered by material 108 whereas 0.6 square centimeters would be covered by holes 110. The metal to vessel ratio can be expressed as a fraction, e.g., 0.4 for this example, or as a percentage, e.g., 40% for this example. To convert, the fraction is multiplied by 100 to obtain the percentage.

Although a fixed metal to vessel ratio is set forth, in other embodiments, the metal to vessel ratio of proximal high metal to vessel ratio zone 118 varies in the longitudinal direction 112 and/or in the circumferential direction 114 along variable zone high metal to vessel ratio stent 100.

As set forth above, the metal to vessel ratio is defined when variable zone high metal to vessel ratio stent 100 and thus proximal high metal to vessel ratio zone 118 is in the final configuration. Variable zone high metal to vessel ratio stent 100 is in the final configuration when in its final unconstrained expanded state, sometimes called at nominal deployment. More particularly, when the diameter of variable zone high metal to vessel ratio stent 100 is approximately equal, e.g., 10% to 20% oversized, to the diameter of the vessel in which variable zone high metal to vessel ratio stent 100 is being deployed and variable zone high metal to vessel ratio stent 100 is at its natural unconstrained length at this diameter, variable zone high metal to vessel ratio stent 100 is in its final state. Generally, once deployed within the vessel at its natural unconstrained length as discussed below, variable zone high metal to vessel ratio stent 100 is in the final configuration.

The final configuration should be contrasted to the constrained configuration of variable zone high metal to vessel ratio stent 100. Variable zone high metal to vessel ratio stent 100 is in a constrained configuration when variable zone high metal to vessel ratio stent 100 is constrained to a reduced diameter, e.g., within a delivery sheath. Further, variable zone high metal to vessel ratio stent 100 is in a constrained configuration when variable zone high metal to vessel ratio stent 100 is constrained to a reduced or expanded length, e.g., by longitudinally compressing or expanding variable zone high metal to vessel ratio stent 100. When in the constrained configuration, either in length, diameter, or both, holes 110 are collapsed resulting in a much higher metal to vessel ratio for variable zone high metal to vessel ratio stent 100 than when variable zone high metal to vessel ratio stent 100 and is in its final configuration.

As discussed further below, e.g., in reference to FIGS. 3-6, the metal to vessel ratio of proximal high metal to vessel ratio zone 118 is sufficiently high to encourage tissue ingrowth around proximal high metal to vessel ratio zone 118.

Generally, the metal to vessel ratio of proximal high metal to vessel ratio zone 118 is within the range of 30 percent to 80 percent (30-80%), more suitably within the range of 35 percent to 60 percent (35-60%). In one particular embodiment, the metal to vessel ratio is 40 percent (40%).

Distal high metal to vessel ratio zone 122 also has a high metal to vessel ratio as defined above. In one embodiment, distal high metal to vessel ratio zone 122 is identical in structure to proximal high metal to vessel ratio zone 118 and thus has the identical high metal to vessel ratio. As discussed further below, e.g., in reference to FIGS. 3-6, the metal to vessel ratio of distal high metal to vessel ratio zone 122 is sufficiently high to encourage tissue ingrowth around distal high metal to vessel ratio zone 122 as well as to provide adequate aneurysm exclusion.

In contrast, central low metal to vessel ratio zone 120 has a low metal to vessel ratio. Generally, the metal to vessel ratio of central low metal to vessel ratio zone 120 is less than 30%. As discussed further below, e.g., in reference to FIGS. 3-6, the metal to vessel ratio of central low metal to vessel ratio zone 120 is sufficiently low to allow perfusion of branch vessels through central low metal to vessel ratio zone 120.

In one embodiment, variable zone high metal to vessel ratio stent 100 is formed of balloon expandable and/or self-expanding metal, e.g., e.g., formed of Nitinol or stainless steel. In one embodiment, variable zone high metal to vessel ratio stent 100 is integral, i.e., a single piece and not a plurality of separate pieces connected together. For example, a cylindrical tube of metal, e.g., Nitinol, is laser cut to form holes 110 therein thus forming variable zone high metal to vessel ratio stent 100. The cylindrical tube of metal can be formed from a metal sheet that is bent and welded in one embodiment. As illustrated in FIG. 2, variable zone high metal to vessel ratio stent 100 has a thickness T, e.g., equal to the thickness of the cylindrical tube from which variable zone high metal to vessel ratio stent 100 is formed.

Variable zone high metal to vessel ratio stent 100 includes a plurality of serpentine rings 124, 126, 128, sometimes called first, second, and third serpentine rings 124, 126, 128, connected together by connector bars 130. Serpentine rings 124, 126, 128 include a zigzag pattern, sometimes called a sinusoidal or an alternating repeating pattern. More particularly, each serpentine ring 124, 126, 128 includes a repeating pattern of proximal apexes 132 and distal apexes 134 connected by struts 136. Proximal apexes 132 and distal apexes 134 are sometimes called peaks and valleys, respectively, or crowns.

More particularly, proximal high metal to vessel ratio zone 118 is formed of serpentine rings 124 connected together by connector bars 130. Central low metal to vessel ratio zone 120 is formed of serpentine rings 126 connected together by connector bars 130. Distal high metal to vessel ratio zone 122 is formed of serpentine rings 128 connected together by connector bars 130.

To provide central low metal to vessel ratio zone 120 with a lower metal to vessel ratio than proximal and distal high metal to vessel ratio zones 118, 122, serpentine rings 126 are larger than serpentine rings 124, 128.

More particularly, each serpentine ring 124, 126, 128 has a wavelength and an amplitude. The wavelength is defined as the distance over which the serpentine ring's shape repeats in circumferential direction 114. The amplitude is defined as the peak deviation of the serpentine ring from its center position in longitudinal direction 112.

Serpentine rings 124 of proximal high metal to vessel ratio zone 118 have a first wavelength $\lambda 1$ and a first amplitude A1. Serpentine rings 126 of central low metal to vessel ratio zone 120 have a second wavelength $\lambda 2$ and a second amplitude A2. Serpentine rings 128 of distal high metal to vessel ratio zone 122 have a third wavelength $\lambda 3$ and a third amplitude A3.

Wavelength $\lambda 2$ and amplitude A2 of serpentine rings 126 of central low metal to vessel ratio zone 120 are larger than wavelength $\lambda 1$ and amplitude A1 of serpentine rings 124 of proximal high metal to vessel ratio zone 118. In accordance with this embodiment, wavelength $\lambda 2$ and amplitude A2 of serpentine rings 126 of central low metal to vessel ratio zone 120 are also larger than wavelength $\lambda 3$ and amplitude A3 of serpentine rings 128 of distal high metal to vessel ratio zone 122.

Figure 3:
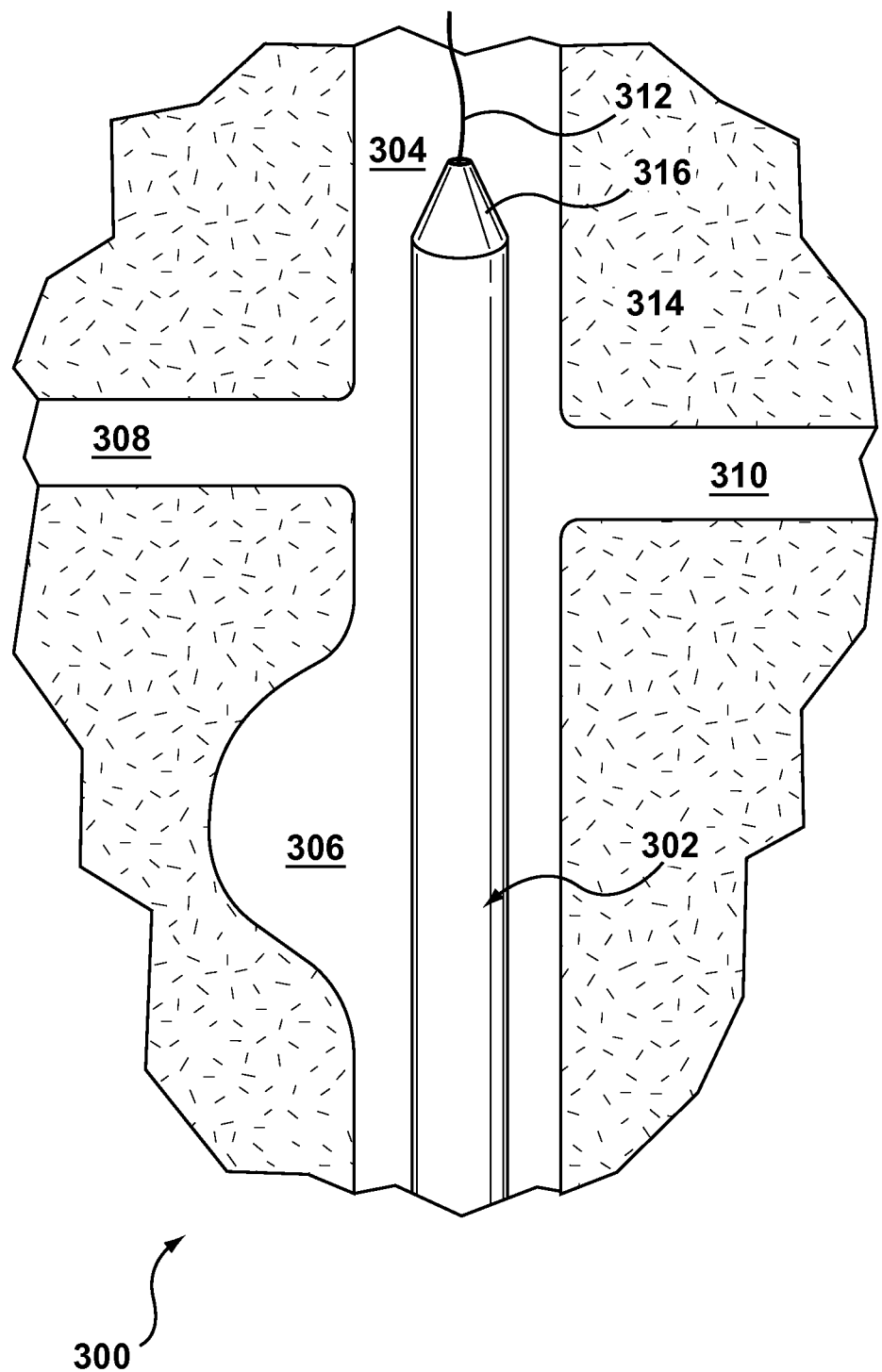
FIG. 3 is a cross-sectional view of a vessel assembly including a delivery system including the variable zone high metal to vessel ratio stent of FIGS. 1 and 2 in accordance with one embodiment.
Figure 4:
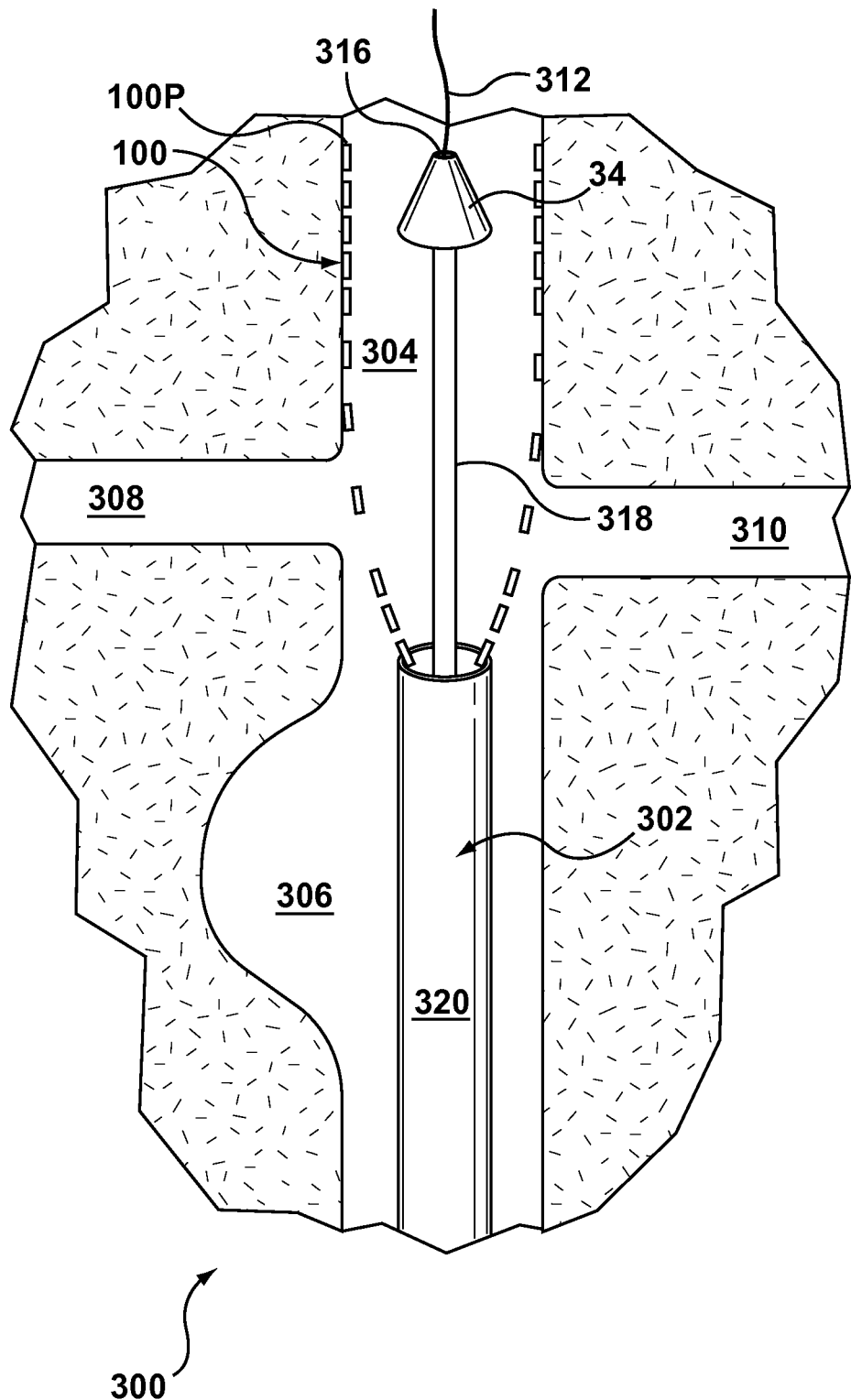
FIG. 4 is a cross-sectional view of the vessel assembly including the delivery system at a later stage of deploying the variable zone high metal to vessel ratio stent of FIGS. 1 and 2 in accordance with one embodiment.

FIG. 3 is a cross-sectional view of a vessel assembly 300 including a delivery system 302 including variable zone high metal to vessel ratio stent 100 of FIGS. 1 and 2 in accordance with one embodiment. FIG. 4 is a cross-sectional view of vessel assembly 300 including delivery system 302 at a later stage of deploying variable zone high metal to vessel ratio stent 100 of FIGS. 1 and 2 in accordance with one embodiment.

Referring now to FIGS. 3 and 4 together, a main vessel 304, e.g., the aorta, includes an aneurysm 306. Variable zone high metal to vessel ratio stent 100, sometimes called a prosthesis, is deployed into main vessel 304 to exclude aneurysm 306 using delivery system 302.

Emanating from main vessel 304 is a first branch vessel 308 and a second branch vessel 310, sometimes called visceral branches of the abdominal aorta. The location of branch vessels 308, 310 vary from patient to patient. Examples of branch vessels 308, 310 include the renal arteries (RA), the superior mesenteric artery (SMA), the brachiocephalic artery, the left subclavian artery, the left common carotid, the celiac trunk, and the hypogastric artery.

Delivery system 302 is advanced to the location of aneurysm 306, e.g., over a guidewire 312, for example as illustrated in FIG. 3. Delivery system 302 includes a tapered tip 314 that is flexible and able to provide trackability in tight and tortuous vessels. Tapered tip 314 includes a lumen 316 allowing for passage of guidewire 312 in accordance with this embodiment. In one embodiment, delivery system 302 includes radiopaque marker(s) that allow visualization of delivery system 302.

To deploy variable zone high metal to vessel ratio stent 100, an inner member 318 of delivery system 302 including tapered tip 314 mounted thereon is held stationary while an outer sheath 320 of delivery system 302 is withdrawn, for example, as illustrated in FIG. 4. Variable zone high metal to vessel ratio stent 100 is radially constrained by outer sheath 320 around inner member 318. Inner member 318 includes a stent stop or other features to prevent variable zone high metal to vessel ratio stent 100 from moving back as outer sheath 320 is withdrawn.

As outer sheath 320 is withdrawn, variable zone high metal to vessel ratio stent 100 is gradually exposed from proximal end 100P to distal end 100D of variable zone high metal to vessel ratio stent 100. The exposed portion of variable zone high metal to vessel ratio stent 100 radially expands to be in conforming surface contact with main vessel 304. More particularly, variable zone high metal to vessel ratio stent 100 opposes the walls of main vessel 304 thus securing variable zone high metal to vessel ratio stent 100 in place.

In one embodiment, variable zone high metal to vessel ratio stent 100 is self-expanding and thus self expands upon being released from outer sheath 320. However, in other embodiments, variable zone high metal to vessel ratio stent 100 is expanded with a balloon or other expansion device.

Although a particular delivery system 302 is illustrated in FIGS. 3, 4 and discussed above, in light of this disclosure, those of skill in the art will understand that any one of a number of delivery systems can be used to deploy variable zone high metal to vessel ratio stent 100 and the particular delivery system used is not essential to this embodiment.

FIG. 5 is a cross-sectional view of vessel assembly 300 of FIGS. 3 and 4 after deployment of variable zone high metal to vessel ratio stent 100 of FIGS. 1 and 2 in accordance with one embodiment. Referring now to FIG. 5, variable zone high metal to vessel ratio stent 100 is in conforming surface contact with main vessel 304. Variable zone high metal to vessel ratio stent 100 is deployed such that variable zone high metal to vessel ratio stent 100 covers, sometimes called jails, ostai (plural of ostium) 322, 324 of branch vessels 308, 310, respectively.

More particularly, proximal high metal to vessel ratio zone 118 is deployed with fixation and sealing to main vessel 304 superior to branch vessels 308, 310 and aneurysm 306, e.g., to healthy tissue of main vessel 304 proximal to branch vessels 308, 310. This minimizes the risk of migration of variable zone high metal to vessel ratio stent 100. Further, this allows fixation and sealing of variable zone high metal to vessel ratio stent 100 to healthy tissue even when aneurysm 306 has a short neck, i.e., when the distance between aneurysm 306 and branch vessels 308, 310 is relatively small, as well as when aneurysm 306 has a highly angulated neck.

Central low metal to vessel ratio zone 120 is deployed directly on ostai 322, 324 of branch vessels 308, 310, respectively. However, as central low metal to vessel ratio zone 120 is highly permeable, blood flows from main vessel 304 through central low metal to vessel ratio zone 120 and into branch vessels 308, 310 thus perfusing branch vessels 308, 310. In one embodiment, branch vessels 308, 310 are continuously perfused during the entire procedure of deploying variable zone high metal to vessel ratio stent 100.

Further, deployment of variable zone high metal to vessel ratio stent 100 is relatively simple thus minimizing the complexity and thus risk of deploying variable zone high metal to vessel ratio stent 100. More particularly, as the entire central low metal to vessel ratio zone 120 is permeable, variable zone high metal to vessel ratio stent 100 is deployed without having to rotationally position variable zone high metal to vessel ratio stent 100 to be aligned with branch vessels 308, 310.

In another embodiment, variable zone high metal to vessel ratio stent 100 includes scallops, i.e., cutouts or openings. These scallops are aligned with ostai 322, 324 of branch vessels 308, 310. Thus, blood flows from main vessel 304 through the scallops and into branch vessels 308, 310 thus perfusing branch vessels 308, 310 and reducing the risk of occlusion thereof.

Further, distal high metal to vessel ratio zone 122 covers and excludes aneurysm 306. More particularly, once variable zone high metal to vessel ratio stent 100 is anchored within main vessel 304, blood flows through main lumen 106 thus excluding aneurysm 306.

Further, distal high metal to vessel ratio zone 122 is deployed with fixation and sealing to main vessel 304 inferior to aneurysm 306, e.g., to healthy tissue of main vessel 304. This further facilitates exclusion of aneurysm 306 while at the same time minimizes the risk of migration of variable zone high metal to vessel ratio stent 100.

In other examples, variable zone high metal to vessel ratio stent 100 is a bifurcated stent, e.g., variable zone high metal to vessel ratio stent 100 is bifurcated to extend into the iliac arteries.

As discussed above, by forming central low metal to vessel ratio zone 120 with a low metal to vessel ratio, branch vessels 308, 310 are adequately perfused through variable zone high metal to vessel ratio stent 100. At the same time, by forming proximal and distal high metal to vessel ratio zones 118, 122 to have a high metal to vessel ratio, tissue ingrowth of main vessel 304 into variable zone high metal to vessel ratio stent 100 is encouraged.

As discussed above, in one embodiment, variable zone high metal to vessel ratio stent 100 is integral, i.e., is a single piece and not a plurality of separate pieces connected together. More particularly, proximal high metal to vessel ratio zone 118, central low metal to vessel ratio zone 120, and distal high metal to vessel ratio zone 122 are all integral parts of variable zone high metal to vessel ratio stent 100. For example, variable zone high metal to vessel ratio stent 100 is laser cut from a tube.

As variable zone high metal to vessel ratio stent 100 is integral, variable zone high metal to vessel ratio stent 100 is deployed in a single operation which reduces procedure time and complexity. This is in stark contrast to deploying multiple stents one within another to vary the metal to vessel ratio of the resulting multi stent arrangement.

Figure 6:
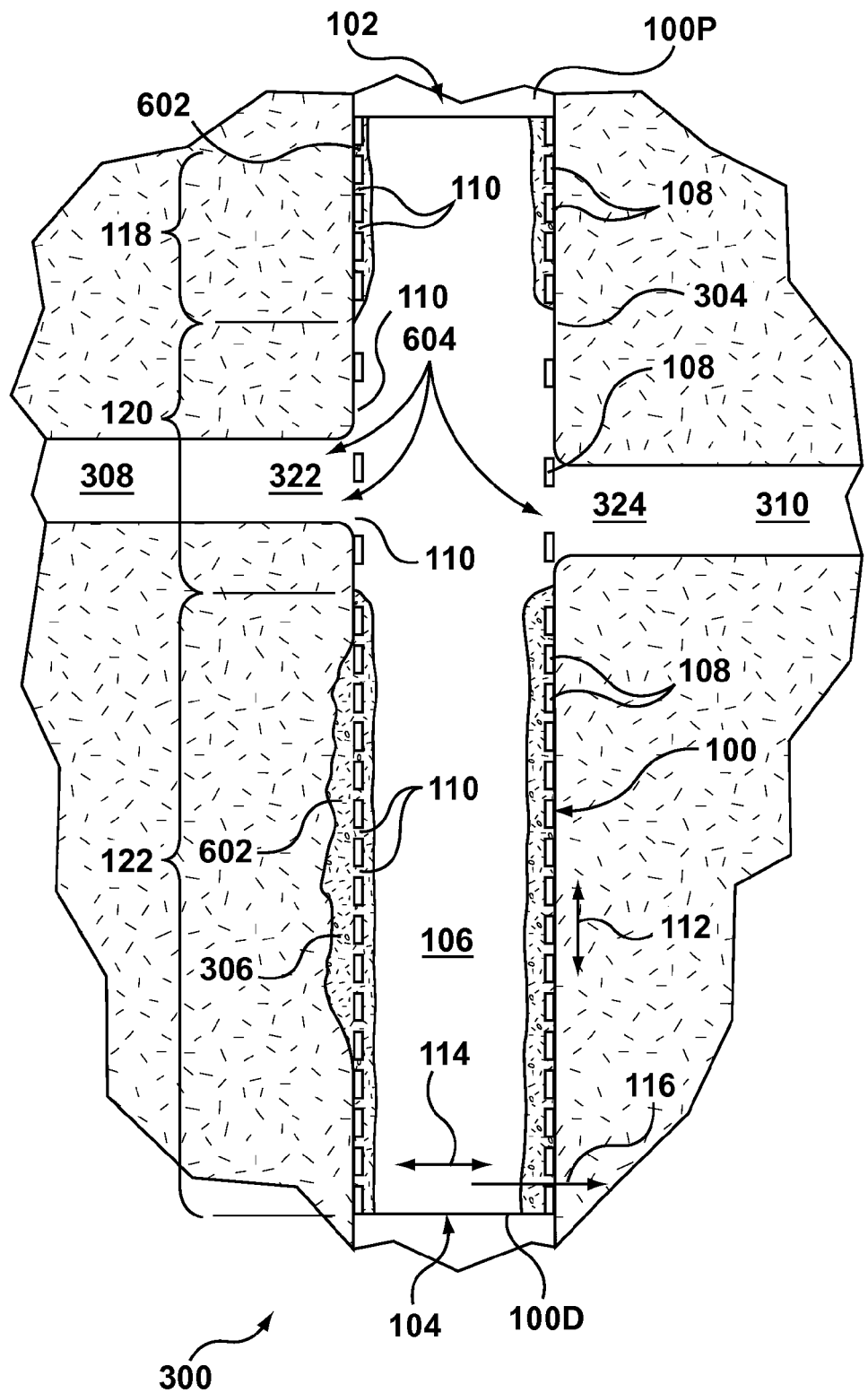
FIG. 6 is a cross-sectional view of the vessel assembly of FIG. 5 illustrating tissue ingrowth into the variable zone high metal to vessel ratio stent.

FIG. 6 is a cross-sectional view of vessel assembly 300 of FIG. 5 illustrating tissue 602 ingrowth into variable zone high metal to vessel ratio stent 100. For example, FIG. 6 illustrates ingrowth of tissue 602 after a period of time, e.g., weeks or months, after the deployment of variable zone high metal to vessel ratio stent 100 into main vessel 304.

Referring now to FIGS. 5 and 6 together, once deployed, tissue 602 of main vessel 304 grows through holes 110 of proximal high metal to vessel ratio zone 118 of variable zone high metal to vessel ratio stent 100. Tissue 602 encases, sometimes called encloses or encapsulates, material 108 of proximal high metal to vessel ratio zone 118 of variable zone high metal to vessel ratio stent 100. Accordingly, proximal high metal to vessel ratio zone 118 is sometimes referred to as a proximal fixation region.

This ingrowth of tissue 602 provides secure fixation and sealing of variable zone high metal to vessel ratio stent 100 to main vessel 304. By providing secure fixation and sealing of variable zone high metal to vessel ratio stent 100 to main vessel 304, the risk of endoleaks into aneurysm 306 and migration of variable zone high metal to vessel ratio stent 100 is minimized.

Further, as illustrated in FIG. 6, tissue 602 does not grow over central low metal to vessel ratio zone 120 of variable zone high metal to vessel ratio stent 100. More particularly, blood flows as indicated by the arrows 604 through holes 110 of central low metal to vessel ratio zone 120 to perfuse branch vessels 308, 310. Accordingly, central low metal to vessel ratio zone 120 is sometimes called a perfusion region.

Further, tissue 602 of main vessel 304 grows through holes 110 of distal high metal to vessel ratio zone 122 of variable zone high metal to vessel ratio stent 100. Tissue 602 encases, sometimes called encloses or encapsulates, material 108 of distal high metal to vessel ratio zone 122 of variable zone high metal to vessel ratio stent 100. Accordingly, distal high metal to vessel ratio zone 122 is sometimes referred to as a distal fixation region.

The ingrowth of tissue 602 into distal high metal to vessel ratio zone 122 restricts expansion of aneurysm 306. In one embodiment, aneurysm 306 is remodeled and essentially eliminated as illustrated in FIG. 6.

In one embodiment, to encourage tissue ingrowth, variable zone high metal to vessel ratio stent 100 includes a surface treatment, e.g., on proximal and distal high metal to vessel ratio zones 118, 122. Illustratively, a thin layer of metal is applied, e.g., by sputtering, physical vapor deposition (PVD), plasma enhanced chemical vapor deposition (PECVD), or other application technique, to variable zone high metal to vessel ratio stent 100 to encourage tissue ingrowth.

Examples of suitable metals include gold, stainless steel, titanium oxide, and/or copper, or combinations thereof are applied to variable zone high metal to vessel ratio stent 100 to encourage tissue ingrowth.

In another embodiment, the surface treatment includes roughening the surface of variable zone high metal to vessel ratio stent 100 to encourage tissue ingrowth. For example, the surface is roughened to have a roughness average (RA) of greater than 1.0 micron (μm). The surface can be roughened by plasma etching, laser etching, sandblasting, a selective etch to preferentially etch one component of variable zone high metal to vessel ratio stent 100 over another, or other surface roughening technique.

In yet another embodiment, the surface treatment includes a growth factor applied to variable zone high metal to vessel ratio stent 100 to enhance tissue ingrowth into variable zone high metal to vessel ratio stent 100. Examples of growth factors include vascular endothelial growth factor (VEGF), platelet-derived growth factor (PDGF), plated-derived epidermal growth factor (PDEGF), fibroblast growth factors (FGFs), basic fibroblast growth factor (bFGF), transforming growth factor-beta (TGF-.beta.), platelet-derived angiogenesis growth factor (PDAF) and autologous platelet gel (APG).

Another example of growth factors include bioactive materials, e.g., a bioactive compound, drug, therapeutic agent or composition having a biological effect in an animal. Bioactive materials include small molecules, peptides, proteins, hormones, DNA or RNA fragments, genes, cells, genetically-modified cells, cell growth promoting compositions, inhibitors of matrix metalloproteinase, fatty acids and autologous platelet gel.

Figure 7:
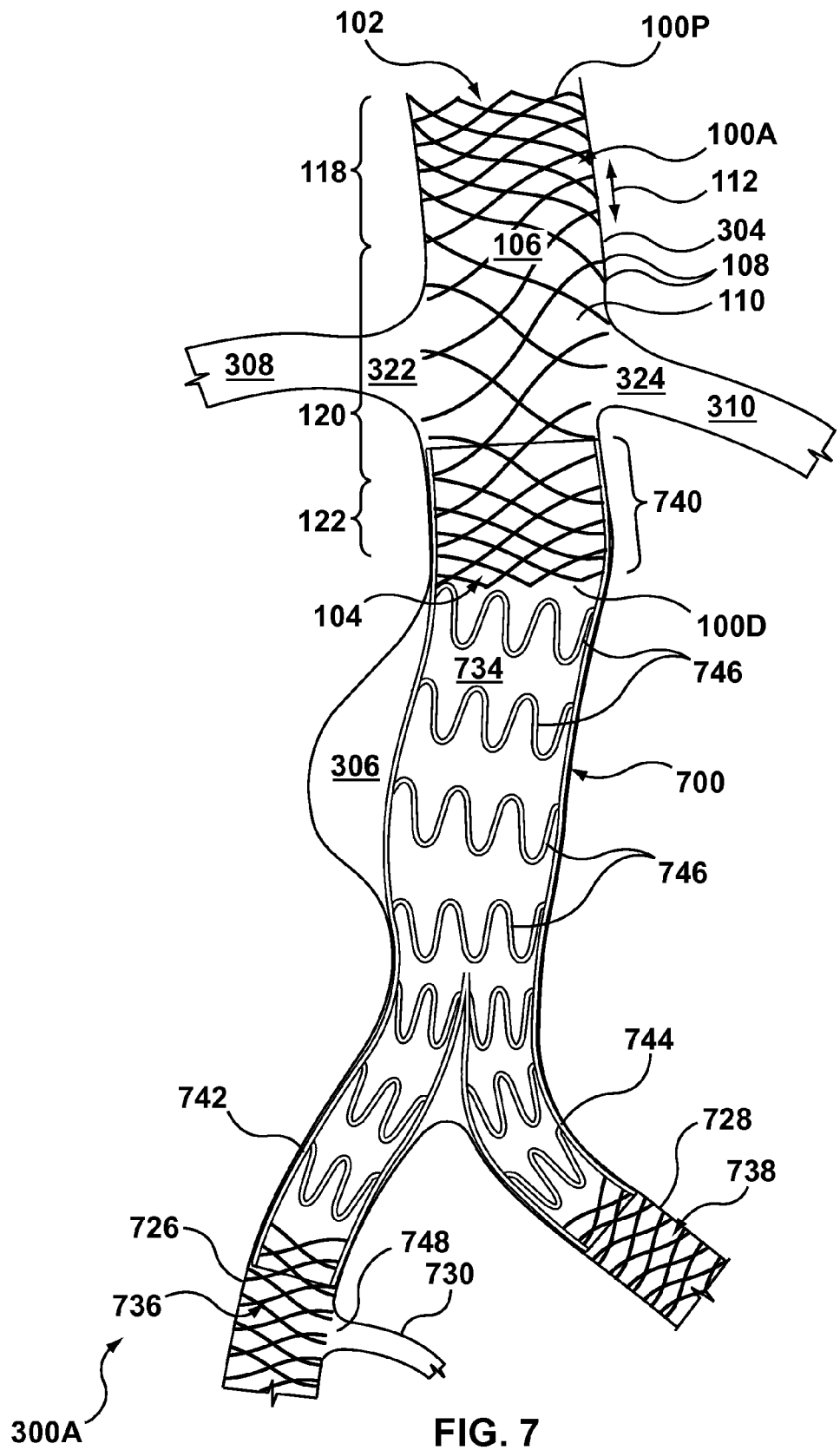
FIG. 7 is a cross-sectional view of a vessel assembly including a variable zone high metal to vessel ratio stent graft in accordance with another embodiment.

FIG. 7 is a cross-sectional view of a vessel assembly 300A including a variable zone high metal to vessel ratio stent graft 700 in accordance with another embodiment. Vessel assembly 300A includes main vessel 304, aneurysm 306, branch vessels 308, 310, ostai 322, 324 as discussed above in reference to FIGS. 3-6.

Further, in accordance with this embodiment, vessel assembly 300A includes first and second bifurcated vessels 726, 728, e.g., the iliac arteries. Vessel assembly 300A also include a bifurcated branch vessel 730, e.g., the hypogastric artery, sometimes called the internal iliac artery, branching from first bifurcated vessel 726.

Variable zone high metal to vessel ratio stent graft 700 includes a variable zone high metal to vessel ratio stent 100A, a bifurcated graft material 734, and stents 736, 738.

Variable zone high metal to vessel ratio stent 100A is similar to variable zone high metal to vessel ratio stent 100 as discussed above in reference to FIGS. 1 and 2 and only the significant differences are discussed below. Variable zone high metal to vessel ratio stent 100A includes a proximal high metal to vessel ratio zone 118, a central low metal to vessel ratio zone 120, and a distal high metal to vessel ratio zone 122.

Illustratively, variable zone high metal to vessel ratio stent 100A is formed of a wire weave. More particularly, proximal high metal to vessel ratio zone 118 is formed of a dense wire weave with fixation and sealing to main vessel 304 superior to aneurysm 306.

The wire weave is longitudinally expanded in longitudinal direction 112 over branch vessels 308, 310 to form central low metal to vessel ratio zone 120 of a spare wire weave. As central low metal to vessel ratio zone 120 is highly permeable, blood flows from main vessel 304 through central low metal to vessel ratio zone 120 and into branch vessels 308, 310 thus perfusing branch vessels 308, 310.

Distal high metal to vessel ratio zone 122 is also formed of a dense wire weave. Distal high metal to vessel ratio zone 122 is attached, e.g., to the outside, of a proximal region 740 of bifurcated graft material 734. Accordingly, distal high metal to vessel ratio zone 122 allows for tissue integration and thus seal enhancement of bifurcated graft material 734 to main vessel 304.

Bifurcated graft material 734 covers and excludes aneurysm 306. Further, bifurcated graft material 734 includes first and second legs 742, 744, sometimes called bifurcations, that extend into first and second bifurcated vessels 726, 728. Optionally, one or more support structures 746, e.g., sinusoidal stent rings, are attached to bifurcated graft material 734 to enhance expansion of bifurcated graft material 734. Although one particular example of bifurcated graft material 734 and support structures 746 is illustrated and discussed, in light of this disclosure, those of skill in the art will understand that other graft designs are used in other embodiments.

First and second stents 736, 738 are attached to legs 742, 744, respectively, of bifurcated graft material 734 to enhance distal fixation of legs 742, 744, to first and second bifurcated vessels 726, 728. In accordance with this embodiment, stents 736, 738 are formed of a wire weave.

As illustrated, stent 736 extends over an ostium 748 of bifurcated branch vessel 730. Blood flows from first bifurcated vessel 726 through stent 736 and into bifurcated branch vessel 730 thus perfusing bifurcated branch vessel 730.

Figure 8:
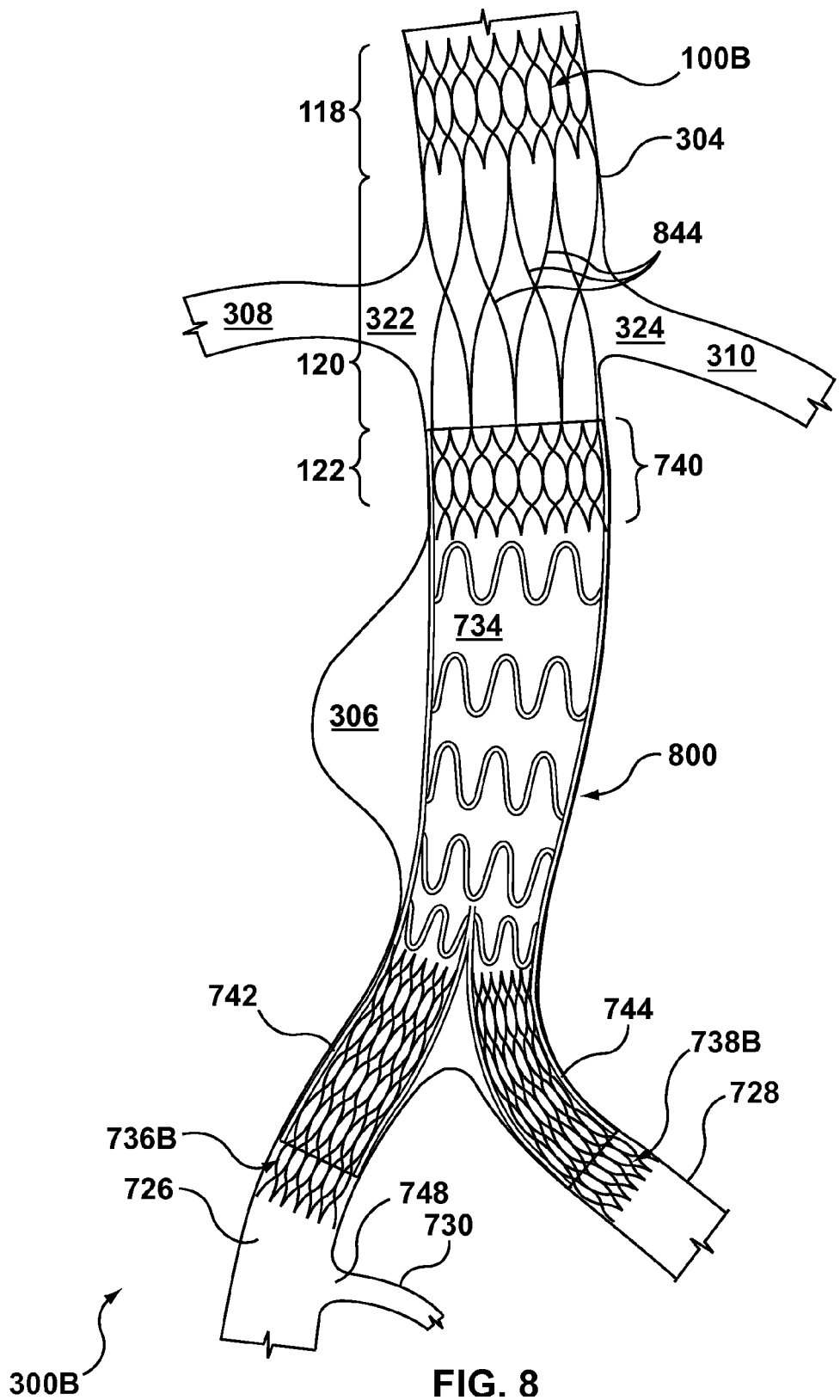
FIG. 8 is a cross-sectional view of a vessel assembly including a variable zone high metal to vessel ratio stent graft in accordance with yet another embodiment.

FIG. 8 is a cross-sectional view of a vessel assembly 300B including a variable zone high metal to vessel ratio stent graft 800 in accordance with yet another embodiment. Vessel assembly 300B includes main vessel 304, aneurysm 306, branch vessels 308, 310, ostai 322, 324, first and second bifurcated vessels 726, 728, bifurcated branch vessel 730 including ostium 748, as discussed above in reference to FIG. 7.

Variable zone high metal to vessel ratio stent graft 800 includes a variable zone high metal to vessel ratio stent 100B, bifurcated graft material 734, and stents 736B, 738B.

Variable zone high metal to vessel ratio stent 100B is similar to variable zone high metal to vessel ratio stent 100A as discussed above in reference to FIG. 7 and only the significant differences are discussed below. Variable zone high metal to vessel ratio stent 100B includes a proximal high metal to vessel ratio zone 118, a central low metal to vessel ratio zone 120, and a distal high metal to vessel ratio zone 122.

Illustratively, variable zone high metal to vessel ratio stent 100B is formed of a laser cut structure and/or a wire formed and crimped structure. Proximal high metal to vessel ratio zone 118, e.g., a high metal to vessel ratio mesh, has fixation and sealing to main vessel 304 superior to branch vessels 308, 310 and aneurysm 306.

Central low metal to vessel ratio zone 120 is formed of long longitudinal connectors 844 that extend over branch vessels 308, 310. As central low metal to vessel ratio zone 120 is highly permeable, blood flows from main vessel 304 through central low metal to vessel ratio zone 120 and into branch vessels 308, 310 thus perfusing branch vessels 308, 310.

Distal high metal to vessel ratio zone 122 is also a high metal to vessel ratio mesh. Distal high metal to vessel ratio zone 122 is attached, e.g., to the outside, of proximal region 740 of bifurcated graft material 734. Accordingly, distal high metal to vessel ratio zone 122 allows for tissue integration and thus seal enhancement of bifurcated graft material 734 to main vessel 304.

Bifurcated graft material 734, as discussed above in reference to FIG. 7, covers and excludes aneurysm 306. Stents 736B, 738B are attached to legs 742, 744, respectively, of bifurcated graft material 734 to enhance distal fixation of legs 742, 744 to first and second bifurcated vessels 726, 728.

In accordance with this embodiment, stents 736B, 738B are formed of a high metal to vessel ratio mesh to promote sealing of legs 742, 744 to first and second bifurcated vessels 726, 728.

As illustrated, stent 736B is proximal to ostium 748 of bifurcated branch vessel 730. Accordingly, blood flows unrestricted from first bifurcated vessel 726 into bifurcated branch vessel 730 thus perfusing bifurcated branch vessel 730.

Although treatment of aneurysm 306 is illustrated in the figures and discussed above, in other embodiments, other vessel defects are treated using devices and methods as described herein. For example, other aortic pathologies such as dissections and penetrating ulcers are treated.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A prosthesis comprising:
   a first high metal to vessel ratio zone having first serpentine rings and defining a high metal to vessel ratio within a range of 30 percent to 80 percent, the first high metal to vessel ratio zone located at a first end of the prosthesis;
   a second low metal to vessel ratio zone having second serpentine rings and defining a low metal to vessel ratio less than 30 percent; and
   a third high metal to vessel ratio zone having third serpentine rings and defining a high metal to vessel ratio within the range of 30 percent to 80 percent, the third high metal to vessel ratio zone located at a second end of the prosthesis;
   wherein the first high metal to vessel ratio zone, the second low metal to vessel ratio zone, and the third high metal to vessel ratio zone are integral, and wherein the second low metal to vessel ratio zone is located between the first high metal to vessel ratio zone and the third high metal to vessel ratio zone.

2. The prosthesis of claim 1 wherein the second serpentine rings are larger than the first serpentine rings.

3. The prosthesis of claim 2 wherein the first serpentine rings have a first wavelength and a first amplitude, and the second serpentine rings have a second wavelength and a second amplitude, the second wavelength being greater than the first wavelength, and the second amplitude is greater than the first amplitude.

4. The prosthesis of claim 3 wherein the third serpentine rings are smaller than the second serpentine rings.

5. The prosthesis of claim 4 wherein the third serpentine rings have a third wavelength and a third amplitude, the second wavelength being greater than the third wavelength, and the second amplitude is greater than the third amplitude.

6. The prosthesis of claim 4 further comprising connector bars connecting the first, second, and third serpentine rings together.

7. The prosthesis of claim 4 wherein the first, second, and third serpentine rings comprise proximal apexes, distal apexes, and struts connecting the proximal apexes and the distal apexes.

8. The prosthesis of claim 1 wherein the first high metal to vessel ratio is within the range of 35 percent to 60 percent.

9. The prosthesis of claim 1 further comprising:
   a surface treatment to encourage tissue ingrowth.

10. The prosthesis of claim 9 wherein the surface treatment comprises a metal.

11. The prosthesis of claim 9 wherein the surface treatment comprises roughening the prosthesis.

12. The prosthesis of claim 9 wherein the surface treatment comprises a growth factor.

13. A delivery system comprising: a prosthesis comprising:
   a first high metal to vessel ratio zone having first serpentine rings and defining a high metal to vessel ratio within a range of 30 percent to 80 percent, the first high metal to vessel ratio zone located at a first end of the prosthesis;
   a second low metal to vessel ratio zone having second serpentine rings and defining a low metal to vessel ratio less than 30 percent;
   a third high metal to vessel ratio zone having third serpentine rings and defining a high metal to vessel ratio within the range of 30 percent to 80 percent, the third high metal to vessel ratio zone located at a second end of the prosthesis;
   wherein the first high metal to vessel ratio zone, the second low metal to vessel ratio zone, and the third high metal to vessel ratio zone are integral, and wherein the second low metal to vessel ratio zone is located between the first high metal to vessel ratio zone and the third high metal to vessel ratio zone; and
   an outer sheath radially constraining the prosthesis.

14. The delivery system of claim 13 further comprising an inner member, the prosthesis being radially constrained around the inner member by the outer sheath.

\* \* \* \* \*